United States Patent
Yee et al.

(10) Patent No.: US 8,876,712 B2
(45) Date of Patent: Nov. 4, 2014

(54) INTRACARDIAC SHEATH STABILIZER

(75) Inventors: Kristopher Yee, San Francisco, CA (US); Francis G. Duhay, Irvine, CA (US); Manouchehr Miraki, Laguna Hills, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 547 days.

(21) Appl. No.: 12/845,584

(22) Filed: Jul. 28, 2010

(65) Prior Publication Data

US 2011/0028797 A1 Feb. 3, 2011

Related U.S. Application Data

(60) Provisional application No. 61/229,675, filed on Jul. 29, 2009.

(51) Int. Cl.
*A61B 1/32* (2006.01)
*A61B 17/02* (2006.01)
*A61B 17/34* (2006.01)

(52) U.S. Cl.
CPC ..... *A61B 17/0206* (2013.01); *A61B 2017/0237* (2013.01); *A61B 17/0293* (2013.01); *A61B 17/3423* (2013.01)
USPC ...................................................... 600/231

(58) Field of Classification Search
CPC ...... A61B 1/32; A61B 17/02; A61B 17/0057; A61B 17/0206
USPC ............ 248/75, 157, 160, 419–430; 600/102, 600/114, 201–246
See application file for complete search history.

(56) References Cited

U.S. PATENT DOCUMENTS 5,267,970 A  12/1993  Chin et al.
5,976,080 A  11/1999  Farascioni (Continued)

FOREIGN PATENT DOCUMENTS

WO  99/37213 A1  7/1999
WO  01/52717 A2  7/2001
WO  02/36032 A1  5/2002

OTHER PUBLICATIONS

Applied Medical, Alexis O Wound Retractor Brochure; date unknown, Jul. 2009 or earlier; 2 pg., Rancho Santa Margarita CA, Applied Medical.

(Continued)

*Primary Examiner* — Christopher Beccia
(74) *Attorney, Agent, or Firm* — AnneMarie Kaiser

(57) ABSTRACT

A surgical stabilizer for use with a surgical site retractor has a base, a bendable arm, and a distal cuff adapted to resiliently hold a tube of an elongated port-access device. The cuff may have a body defining a partial enclosure within which is held a highly flexible gasket having a slit for resiliently receiving the tube. The surgical site retractor may have a collapsible ring and a flexible outer portion attached thereto, the ring being sized to pass through an intercostal incision and expand therein under adjacent ribs to prevent removal, and the flexible outer portion extending out of the incision and drawing over the stabilizer base to mutually secure the retractor and base. The port-access tube may be for a heart valve delivery system using an elongated port-access device for transapically delivering a prosthetic heart valve to the aortic valve annulus. A method involves partly installing the surgical site retractor, anchoring the base of the stabilizer with the flexible outer portion, deploying the port-access tube from outside the body through the incision and through a puncture in the heart wall, and resiliently capturing a tube of the port-access within the partial enclosure of the stabilizer cuff. A second bendable arm on the base having a clip may be used to hold still a proximal end of the port-access device.

14 Claims, 14 Drawing Sheets

(56) References Cited

U.S. PATENT DOCUMENTS

| | | | |
|---|---|---|---|
| 5,980,455 A | | 11/1999 | Daniel et al. |
| 6,013,027 A | * | 1/2000 | Khan et al. .................. 600/201 |
| 6,251,065 B1 | | 6/2001 | Kochamba et al. |
| 6,309,349 B1 | | 10/2001 | Bertolero et al. |
| 6,371,906 B1 | | 4/2002 | Borst et al. |
| 6,565,508 B2 | | 5/2003 | Scirica et al. |
| 6,581,889 B2 | | 6/2003 | Carpenter et al. |
| 6,592,573 B2 | | 7/2003 | Castaneda et al. |
| 6,673,013 B2 | | 1/2004 | Benetti et al. |
| 6,701,930 B2 | | 3/2004 | Benetti et al. |
| 6,814,700 B1 | | 11/2004 | Mueller et al. |
| 6,866,628 B2 | | 3/2005 | Goodman et al. |
| 7,048,683 B2 | | 5/2006 | Borst et al. |
| 7,201,716 B2 | | 4/2007 | Boone et al. |
| 7,219,671 B2 | | 5/2007 | Benetti |
| 7,226,448 B2 | | 6/2007 | Bertolero et al. |
| 7,237,555 B2 | | 7/2007 | Kochamba et al. |
| 7,438,680 B2 | | 10/2008 | Guenst et al. |
| 7,476,199 B2 | | 1/2009 | Spence et al. |
| 7,497,823 B2 | | 3/2009 | Parihar et al. |
| 7,497,824 B2 | | 3/2009 | Taylor |
| 7,559,125 B2 | * | 7/2009 | Cofer .............................. 24/487 |
| 2005/0010197 A1 | | 1/2005 | Lau et al. |
| 2007/0208223 A1 | | 9/2007 | Julian et al. |
| 2008/0092349 A1 | | 4/2008 | Cofer |
| 2008/0139879 A1 | * | 6/2008 | Olson et al. ................... 600/37 |
| 2012/0116172 A1 | | 5/2012 | Butler et al. |

OTHER PUBLICATIONS

Cardiovations, Port-Access Operative Procedure Manual; date unknown, Jul. 2009 or earlier; 21 pg., Cardiovations.

Edwards Lifesciences; Cardiovations, Heartport Soft Tissue Retractor; Instructions for Use; Mar. 2008; 2 pg., Irvine CA, Edwards Lifesciences.

ESTECH, Superior Stabilization and Positioning for Off-Pump Procedures; Feb. 15, 2006; 2 pg., San Ramon CA, ESTECH.

Marquet GmbH & Co. KG, Products—Acrobat SUV Vacuum Stabilizer; Apr. 28, 2009; 1 pg., Wayne NJ, Marquet GmbH & Co. KG.

Marquet GmbH & Co. KG, Products—Acrobat V Vacuum Stabilizer; Apr. 28, 2009; 1 pg., Wayne NJ, Maquet GmbH & Co. KG.

Medtronic, Beating Heart Technologies Portfolio: Conventional and Minimally Invasive Therapies; date unknown, 2007 or earlier; 12 pg., Minneapolis MN, Medtronic.

Medtronic, The Octopus Evolution Tissue Stabilizer; date unknown, 2006 or earlier; 2 pg., Minneapolis MN, Medtronic.

\* cited by examiner

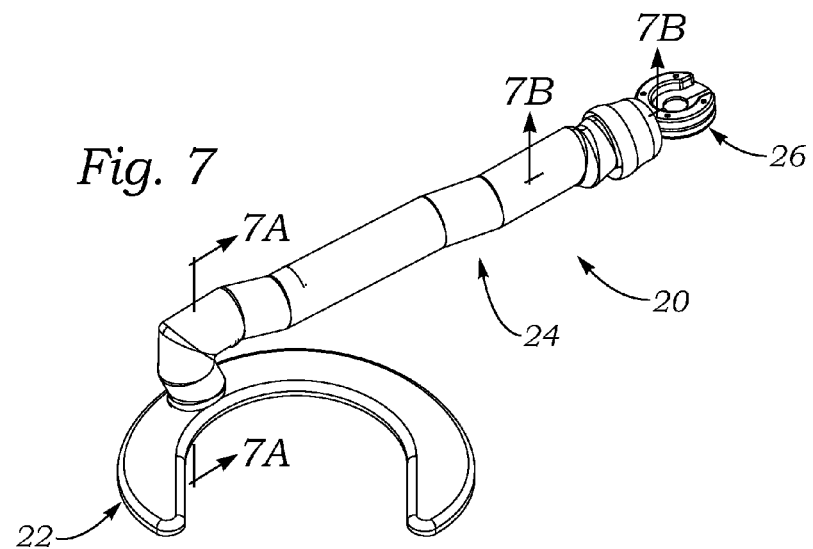
*Fig. 7*
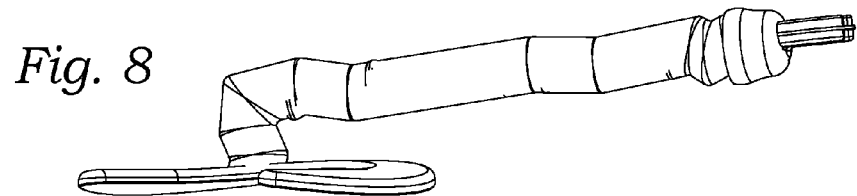
*Fig. 8*
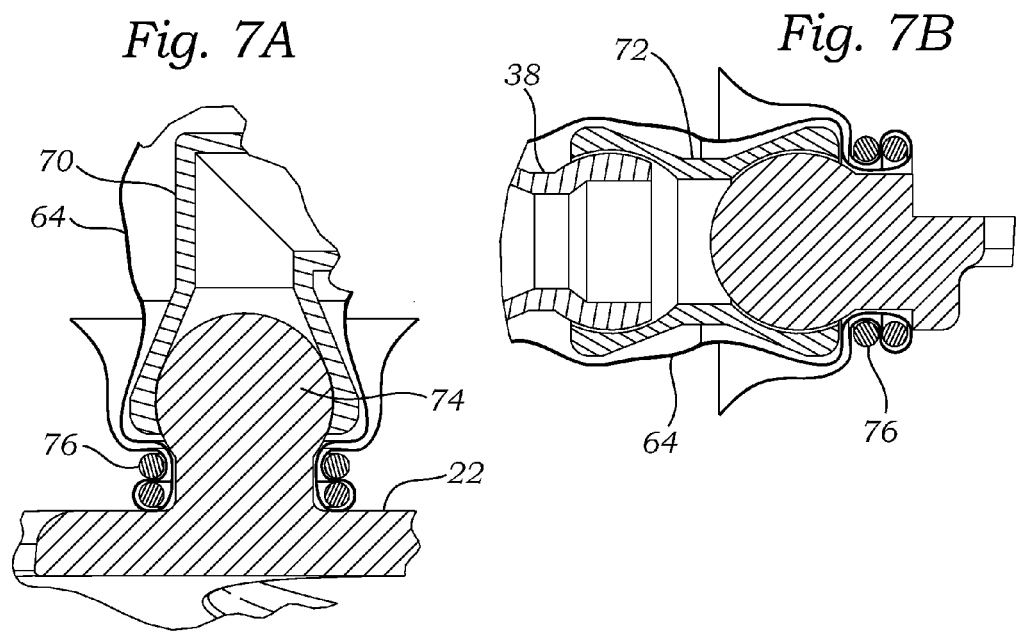
*Fig. 7A*
*Fig. 7B*

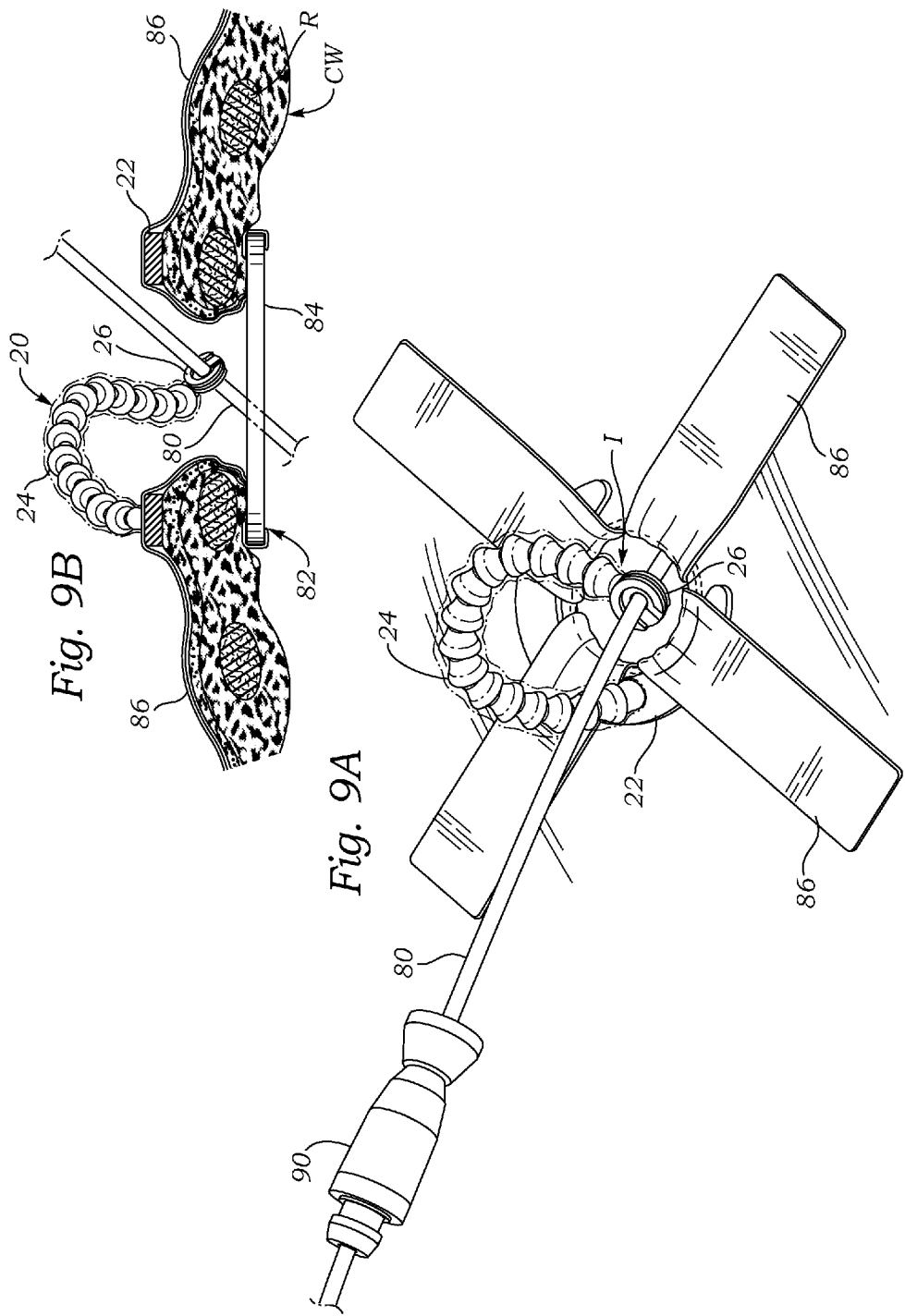

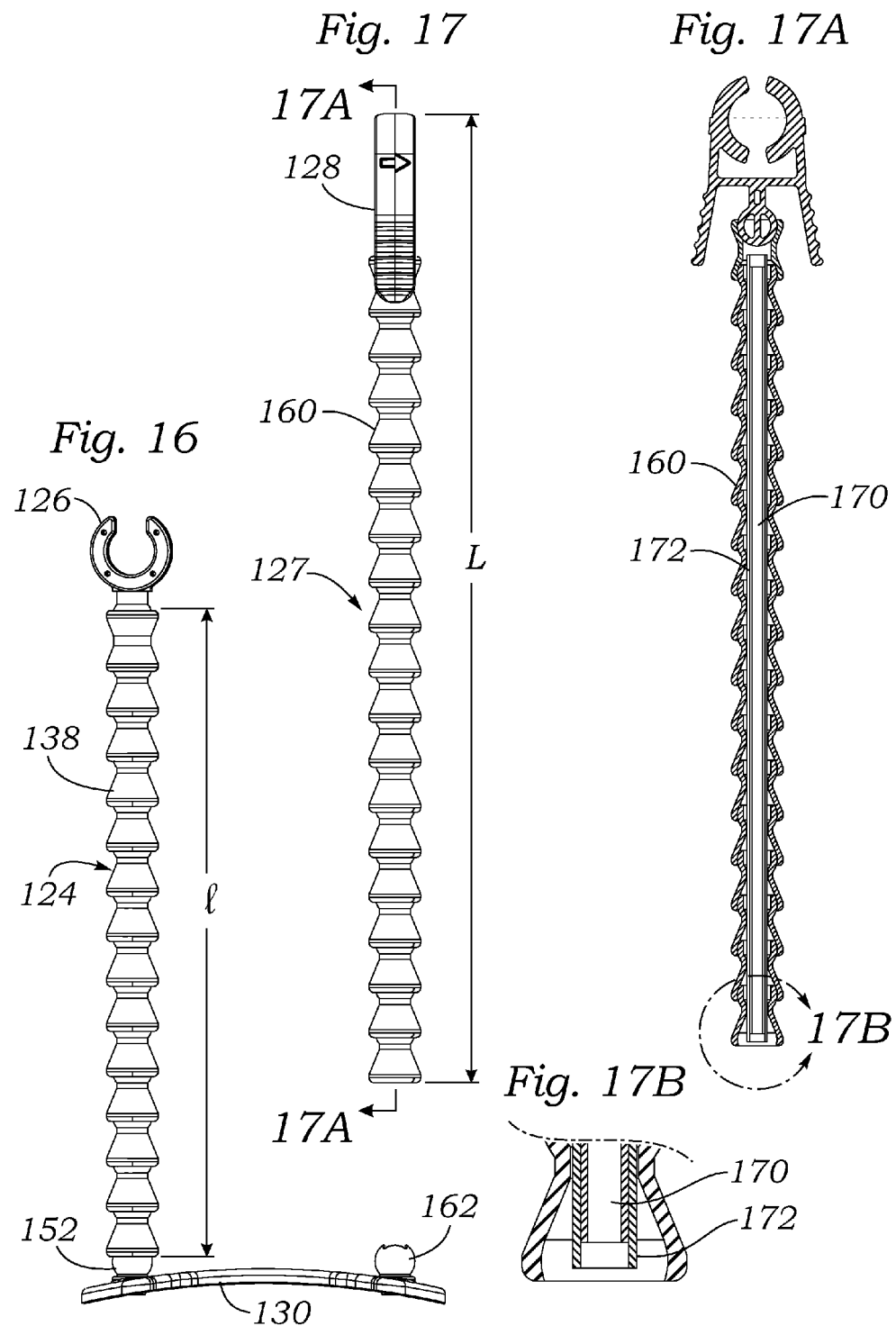

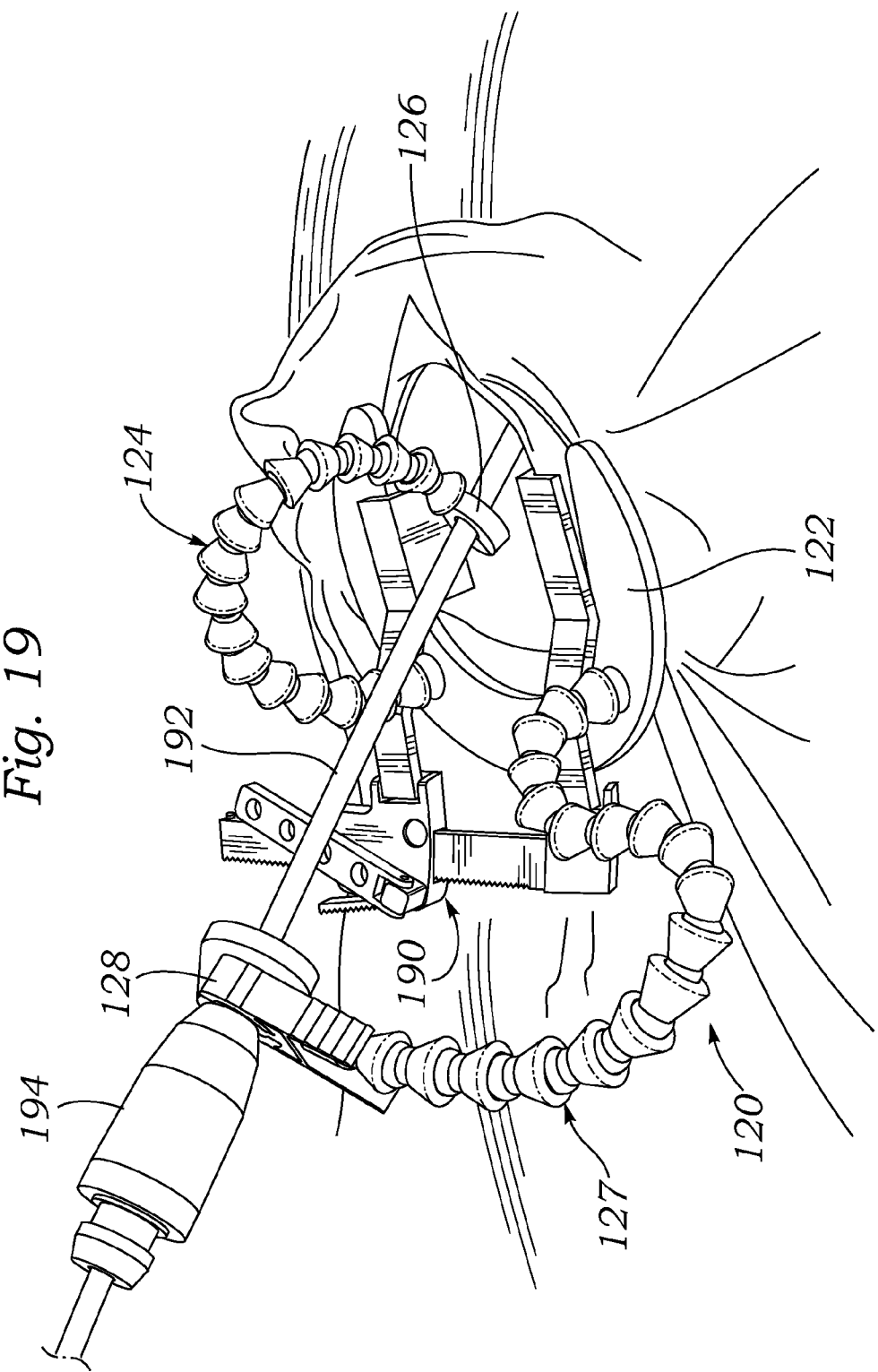

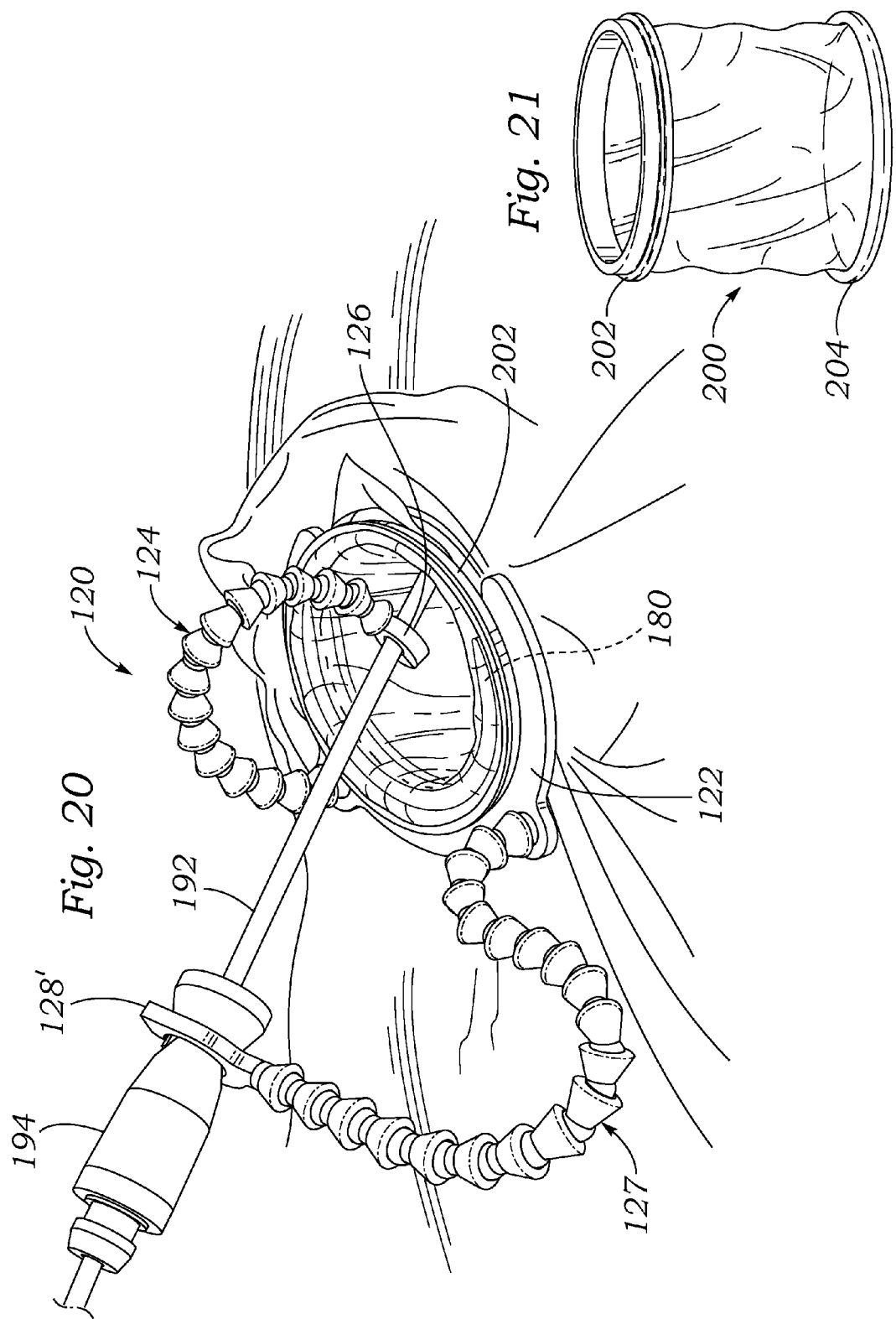

INTRACARDIAC SHEATH STABILIZER

RELATED APPLICATIONS

The present invention application claims priority under 35 U.S.C. §119(e) to U.S. provisional application No. 61/229,675 filed Jul. 29, 2009.

FIELD OF THE INVENTION

The present invention relates to methods and systems for stabilizing tubular surgical port-access devices and, more specifically, during a cardiac procedure.

BACKGROUND OF THE INVENTION

Heart valve disease continues to be a significant cause of morbidity and mortality, resulting from a number of ailments including rheumatic fever and birth defects. Recent statistics show that valvular heart disease is responsible for nearly 20,000 deaths each year in the United States, and is a contributing factor in approximately 42,000 deaths. Currently, the primary treatment of aortic valve disease is valve replacement. Worldwide, there are approximately 300,000 heart valve replacement surgeries performed annually.

Coronary artery disease also remains a leading cause of morbidity and mortality and manifests in a number of ways. For example, disease of the coronary arteries can lead to insufficient blood flow resulting in the discomfort and risks of angina and ischemia. In severe cases, acute blockage of coronary blood flow can result in myocardial infarction, leading to immediate death or damage to the myocardial tissue.

A number of interventional approaches have been developed for treating heart valve and coronary artery disease. For instance, annuloplasty rings have been developed in various shapes and configurations over the years to correct mitral regurgitation and other conditions which reduce the functioning of the valve. Heart valve replacement may be indicated when there is a narrowing of a native heart valve, commonly referred to as stenosis, or when the native valve leaks or regurgitates, such as when the leaflets are calcified. When replacing the valve, the native valve may be excised and replaced with either a biologic or a mechanical valve. Coronary blockage can often be treated endovascularly using techniques such as balloon angioplasty, atherectomy, or stents.

Most interventional techniques are conducted under general anesthesia and require that the patient's sternum be opened and the chest be spread apart to provide access to the heart. The first 2-3 days following surgery are spent in an intensive care unit where heart functions can be closely monitored. The average hospital stay is between 1 to 2 weeks, with several more weeks to months required for complete recovery. While often very effective, the use of open-heart surgery to perform cardiac procedures is a highly traumatic to the patient.

Recently, minimally invasive surgical techniques and procedures to perform coronary artery bypass grafting (CABG) and other traditionally open-chest cardiac surgical procedures are gaining acceptance. A wide variety of laparoscopic, arthroscopic, endovascular, and other surgical therapies have been developed. These procedures generally utilize trocars, cannulas, catheters, or other tubular sheaths to provide an artificial lumen, through which specialized tools are inserted and manipulated by the surgeon.

Some researchers propose implanting prosthetic heart valves at the aortic annulus using a direct-access transapical (through the left ventricular apex) approach (e.g., U.S. Patent Publication No. 2006-0074484). The left ventricular apex LVA is directed downward, forward, and to the left (from the perspective of the patient). The apex typically lies behind the fifth left intercostal space (or between the fourth and fifth), 8 to 9 cm from the mid-sternal line, and about 4 cm below and 2 mm to the medial side of the left mammary papilla. Access to the left ventricle may therefore be attained through an intercostal incision positioned over the fifth left intercostal space. Such an approach is often termed a "mini-thoracotomy," and lends itself to surgical operations on the heart carried out using one or more short tubes or "ports"—thus, the operations are often referred to as "port-access" procedures. Such direct-access or "port access" techniques though less invasive than conventional open heart surgery are not called "minimally-invasive," as that term is now primarily used to refer to valves delivered using elongated catheters via the vasculature (i.e., endovascularly).

Dehdashtian in U.S. Patent Publication No. 2007-0112422 discloses a port-access delivery system for transapical delivery of a prosthetic heart valve including a balloon catheter having a steering mechanism thereon that passes through an access device such as an introducer. The surgeon forms a puncture in the apex with a needle, advances a guidewire, then a dilator, and finally the introducer. Edwards Lifesciences sells the Sapien™ Heart Valve that may be inserted transapically with the Ascendra™ delivery system, much like the system disclosed in Dehdashtian.

Often, direct- or port-access techniques are conducted or proposed for off-pump, or beating heart procedures. The advantages of eliminating open-heart procedures and cardiopulmonary bypass are evident. Challenges remain in stabilizing various instruments used during these procedures. For example, a number of devices are available that directly contact the heart muscle for stabilizing an area around a cardiac artery for CABG procedures, most notable the OCTOPUS and URCHIN devices from Medtronic, and ACROBAT and XPOSE devices from Maquet. These systems typically include a soft contact member having suction that brackets a coronary artery, or grabs and manipulates an area of the heart for better access. These systems are mostly concerned with holding still a discrete surface area of the heart for direct operation thereon, and are not designed for operations carried out by instruments that extend within the beating heart, i.e., for intracardiac procedures.

In view of drawbacks associated with previously known techniques for stabilizing certain port-access procedures, improved methods and apparatuses are needed.

SUMMARY OF THE INVENTION

Preferred embodiments of the present application provide a stabilizer for a port-access device having a tube that helps hold the tube from excessive movement while avoiding undue trauma to the heart muscle. In particular, the present application discloses stabilizers that assist a port-access heart valve delivery system for delivery of a prosthetic (i.e., replacement) heart valve through the heart wall to a native valve site.

A surgical stabilizer for use with a surgical site retractor, including a base defining a periphery with a size that enables it to be held against an exterior chest wall by the surgical site retractor and around a chest incision. A first arm capable of being bent into and retaining a variety of shapes attaches to extends away from the base. A cuff attaches to the arm opposite the base, the cuff having a stiff C-shaped partial ring and a flexible gasket held across an area defined within the C-shaped partial ring. The gasket defines a slit directed toward an open mouth of the C-shaped partial ring, the open mouth being sized larger than an elongated port-access device having a tube such that the cuff can be pressed around the tube, or vice versa, with the tube entering the slit and being resiliently held by the gasket.

The cuff gasket preferably defines an inner aperture smaller than the C-shaped partial ring, the slit connecting to the inner aperture. The cuff C-shaped partial ring also may include a C-shaped lower member attached to a C-shaped upper member, with the gasket sandwiched therebetween. Desirably, one of the lower member and upper member is provided with a ball or socket for a ball and socket junction with the arm. The lower member and the upper member are preferably held together with a plurality of securing pins that pass through holes in the gasket. In one embodiment, the base defines a C-shaped body that may include an upper face and a slightly concave lower contact face, and/or the C-shaped body may have an outer surface of soft polymer with an inner malleable member able to conform to three-dimensional surfaces.

Another aspect of the application is a surgical stabilizer and surgical site retractor combination for assisting an intracardiac procedure through an incision. The surgical site retractor includes a collapsible ring and a plurality of elongate flexible tabs attached thereto. The ring is sized to pass through an intercostal incision and expand therein under adjacent ribs to prevent removal, with the elongate tabs extending out of the incision on at least two opposing sides. The surgical stabilizer has a base defining a periphery larger than the incision surrounding a central opening, the base being constrained outside of the chest wall by the flexible tabs of the retractor. The stabilizer further includes an arm attached to the base capable of being bent into a variety of shapes and a cuff attached to the arm opposite the base. The cuff has a stiff body forming a partial enclosure with an open mouth and a flexible gasket held across an area defined within the partial enclosure, the gasket having a slit directed toward the open mouth. The variations on the cuff and base described above may also apply. In one embodiment, the flexible tabs comprise flat strips of absorbent material, and/or may be flat strips of an elastomeric or semi-elastomeric material.

A further aspect described herein provides a combination of devices for performing an intracadiac procedure through an intercostal incision in a chest wall. The combination features a surgical site retractor and a surgical stabilizer having a base constrained outside of the chest wall adjacent the intercostal incision by the retractor. The stabilizer also includes an arm attached to the base and capable of being bent into a variety of shapes and a cuff attached to the arm opposite the base. The cuff has a stiff body forming a partial enclosure with a flexible gasket defined within the partial enclosure. A port-access device having a tube sized to pass from outside the chest wall through the intercostal incision and through a puncture in the heart wall is resiliently held within the partial enclosure of the cuff by the flexible gasket. The surgical site retractor may be a "soft" retractor that includes a collapsible ring and a plurality of elongate flexible tabs attached thereto. The ring is sized to pass through the intercostal incision and expand therein under adjacent ribs to prevent removal, and the elongate tabs extending out of the incision on at least two opposing sides. Or, the soft retractor may include inner and outer resilient rings, one of which passes through the intercostal incision and expands therein under adjacent ribs, and the other which is pulled over and held to a portion of the stabilizer base, thus mutually securing both elements.

A method for performing an intracadiac procedure through an intercostal incision is described herein. The method includes:

partly installing a surgical site retractor by collapsible a ring and passing it through the intercostal incision and permitting it to expand therein under adjacent ribs to prevent removal;

placing a base of a surgical stabilizer outside of the chest wall and adjacent the incision;

fully installing the surgical site retractor and constraining the base by draping a flexible portion out of the incision and over at least a portion of the stabilizer base to mutually secure the retractor and base;

deploying a port-access device having a tube from outside the body through the incision and through a puncture in the heart wall; and resiliently capturing the port-access device within a partial enclosure of a cuff of the stabilizer located on a distal end of a bendable positioning arm attached to the base thereof.

Another aspect of the invention is a dual-arm surgical stabilizer for use with a surgical site retractor and an elongated port-access device having a tube. The stabilizer includes a base defining a periphery having a size that enables it to be held against an exterior chest wall by the surgical site retractor and around a chest incision. A first arm attached to and extending away from the base is capable of being bent into and retaining a variety of shapes, and has a distal cuff attached thereto opposite the base. The cuff has a partial outer ring sized to receive therein the tube of the port-access device and an inner flexible gasket adapted to resiliently capture the tube within the partial outer ring. A second arm attached to and extending away from the base at a location different than the first arm is also capable of being bent into and retaining a variety of shapes. A distal clip attached to the second arm opposite the base is adapted to clamp onto a part of the port-access device. The second arm is desirably longer and less easily bent than the first arm. Both the first and second arms may be formed with a plurality of segments connected in series and capable of swiveling with respect to one another. The second arm may also have a malleable element extending through aligned throughbores in the segments substantially the entire length of the second arm. Additionally, a frictional interface tube may be sized to closely surround the malleable element and fit closely within the aligned throughbores. In one embodiment, the malleable element is a malleable tube and the frictional interface tube is an elastomer.

In a preferred embodiment of the dual-arm stabilizer, the partial outer ring of the cuff is C-shaped and the inner flexible gasket is held across an area defined within the C-shaped partial ring. The gasket has a slit directed toward an open mouth of the C-shaped partial ring, and the open mouth is sized larger than the tube of the port-access device such that the cuff can be pressed around the tube, or vice versa, with the tube entering the slit and being resiliently held by the gasket. The base preferably defines a malleable C-shaped body with an upper face and a slightly concave lower contact face.

Another aspect of the present application is a combination of devices for performing an intracardiac procedure through a chest incision comprising a surgical site retractor for holding open the chest incision. A surgical stabilizer including a malleable base having a periphery defining therein an open area larger than the chest incision is adapted to be constrained outside of the chest wall by the retractor surrounding the chest incision. The stabilizer further includes a first bendable arm attached to the base and capable of being bent into a variety of shapes. A distal cuff attaches to the arm opposite the base. The cuff has a stiff body forming a partial enclosure with an open mouth and a flexible gasket within the partial enclosure, the gasket being open toward the open mouth to receive and resiliently retain a tubular body therein.

In the aforementioned combination, the surgical site retractor may be a soft retractor having a collapsible ring sized to pass through an intercostal incision and expand therein under adjacent ribs to prevent removal, and a flexible portion that extends out of the incision and drapes over at least a portion of the stabilizer base to mutually secure the retractor and base. For example, the flexible portion of the retractor may include a plurality of flat strips of absorbent material. Alternatively, the flexible portion of the retractor is an outer resilient ring joined to the collapsible ring with a flexible tube, and the stabilizer base includes a raised lip around an inner edge surrounding the open area, the lip being sized such that the outer resilient ring may be lifted over and retained thereby. The raised lip may be a C-shaped adapter removably attached to the base.

The combination may further including a second arm attached to and extending away from the base at a location different than the first arm and capable of being bent into and retaining a variety of shapes. A distal clip attached to the second arm opposite the base is adapted to clamp onto a surgical device. Preferably, wherein the second arm is longer and less easily bent than the first arm. In one embodiment, both the first and second arms are formed with a plurality of segments connected in series and capable of swiveling with respect to one another, and wherein the second arm further includes a malleable element extending through aligned throughbores in the segments substantially the entire length of the second arm.

The combination may also include a port-access device including a tubular sheath, wherein the partial outer ring of the distal cuff is C-shaped and the inner flexible gasket is held across an area defined within the C-shaped partial ring. An open mouth of the C-shaped partial ring is sized larger than the tubular sheath of the port-access device and the gasket is open toward the open mouth to receive and resiliently retain the tubular sheath therein.

A further understanding of the nature and advantages of the present invention are set forth in the following description and claims, particularly when considered in conjunction with the accompanying drawings in which like parts bear like reference numerals.

BRIEF DESCRIPTION OF THE DRAWINGS

Features and advantages of the present invention will become appreciated as the same become better understood with reference to the specification, claims, and appended drawings wherein:

FIGS. 7 and 8 are perspective views of the stabilizer of FIG. 1 with a protective barrier;

FIGS. 7A and 7B are sectional views through proximal and distal ends of an articulated arm of the stabilizer of FIG. 1 showing ball and socket joints for maximum adjustability;

FIGS. 9A and 9B are perspective and sectional views of a surgical procedure carried out with a port-access sheath through an intercostal incision and using the stabilizer of FIG. 1;

FIG. 16 is an elevational view of a part of the stabilizer of FIG. 14A with a longer stabilizing arm disconnected;

FIG. 17 is an elevational view of the longer stabilizing arm disconnected from the stabilizer of FIG. 14A;

FIG. 17A is a longitudinal sectional view of the longer stabilizing arm taken along the line 17A-17A in FIG. 17, and FIG. 17B is an enlargement of one end thereof;

FIG. 19 is a perspective view of a surgical procedure carried out with a port-access sheath through an intercostal incision and using the stabilizer of the FIG. 14A in conjunction with a metal chest spreader;

FIG. 20 is a perspective view of a surgical procedure carried out with a port-access sheath through an intercostal incision and using the stabilizer of the FIG. 14 in conjunction with a flexible wound retractor; and FIG. 21 is an elevational view of the flexible wound retractor of FIG. 20.

DETAILED DESCRIPTION OF THE PREFERRED EMBODIMENTS

Figure 1:
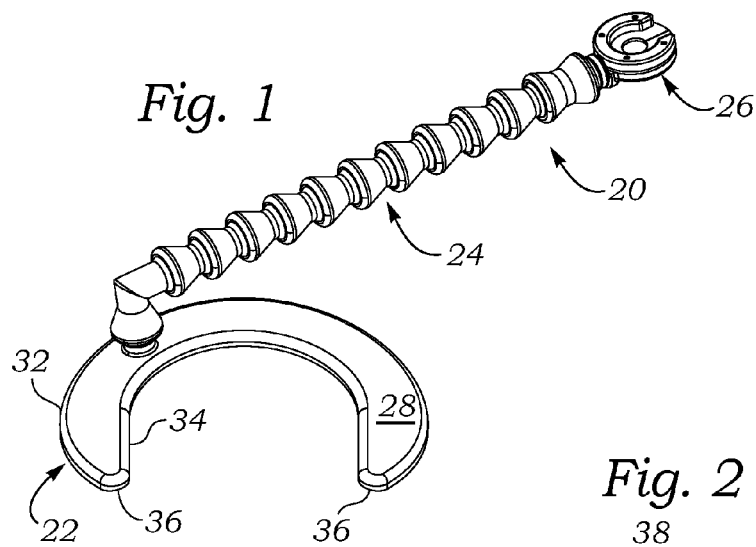
FIGS. 1-4 are perspective views of an exemplary stabilizer of the present application shown without a protective barrier to illustrate a single articulated arm.

In a preferred embodiment of the present invention, a surgeon implants a prosthetic heart valve over the existing native leaflets, which are typically calcified. There are procedures and devices for removing calcified leaflets, but the risks associated therewith, including a release of calcific material into the bloodstream, are not insignificant. Therefore, a heart valve replacement procedure that installs the prosthetic heart valve directly over and contains the native leaflets is preferred.

An exemplary embodiment of a port-access stabilizer 20 is shown in FIGS. 1-8 and essentially comprises a base 22, an articulated arm 24 attached thereto, and a stabilizing cuff 26 attached to the arm opposite the base. The base 22 provides a structural brace adapted to be held by or adjacent to an existing stationary anchor in the surgical field, while the cuff 26 couples to a mid-portion of a tubular port-access device, such as an introducer sheath, and provides stability thereto.

A "stationary anchor in the surgical field" includes a number of different brackets and retractors, an exemplary one of which is shown and explained below. More broadly, the term "stationary" refers to an object decoupled from the motion of the beating heart, including the floor, ceiling or even the patient, such as a portion of the skeletal system of the patient, e.g. the sternum. As will be seen below, a preferred form of the base 22 is a relatively soft and contoured member adapted to be held against the exterior chest wall autonomously or by an existing retractor to provide sufficient stability in three dimensions to the connected arm 24. One preferred method of positioning the base 22 is subjacent to a soft tissue retractor (e.g., Edwards Cardiovations, Applied Medical Alexis), or to a rigid metal spreader-type retractor (e.g., Estech, Finni). However, the base 22 could be adapted to be held against a clamp, retractor, or other such structure adjacent to the surgical field, and should not be considered limited otherwise unless claimed as such.

In its illustrated form, as seen in FIGS. 1-5, the base 22 comprises a C-shaped body having a somewhat planar cross-section with an upper face 28, a lower or contact face 30, a convex outer edge 32, and a concave inner edge 34. The outer edge 32 and inner edge 34 converge in two tips 36. The base 22 is formed of a polymer, and preferably has a relatively soft outer polymer surface and an inner malleable member, such as an elastomeric coated metal like a silicone coated Stainless Steel. Alternatively, the base 22 could be made of Acrylonitrile-Butadiene-Styrene (ABS). The base 22 desirably fits between a soft tissue retractor and the patient's chest wall, and as such benefits from flexibility, softness, and either a contoured shape or the ability to conform to three-dimensional surfaces. In a preferred embodiment, the C-shaped body is a rubber coated metal with a slightly concave curvature toward the contact face 30, that can be shaped as needed per application, as shown in the figures.

The articulated arm 24 may be provided in a number of different forms that provide rigidity or stability to a tubular implement held by the stabilizer 20, while also enabling easy manipulation to reposition the implement. Articulated arms are well known in the art, and the illustrated embodiment includes a plurality of linked segments 38 that are coupled through a ball joint or other similar three-dimensional structural connection. Of course, a simple malleable arm may also be used with some loss of fine control, but the purpose of three-dimensional variation remains. In short, the illustrated articulated arm 24 is shown as an example only, and many variations are possible. In a preferred embodiment, adjustments can be made to the articulation/positioning arm 24 at any time without a loosening/locking mechanism. Furthermore, one articulated arm 24 may be used in the stabilizers disclosed herein, as seen in FIGS. 1-5, or two or more may be provided for greater stability as described below.

The articulated arm 24 comprises segments 38 that snap together, with each contributing a compressive force against adjacent segments to maintain constant friction. This friction between segments gives the arm 24 its ability to resist radial, axial, and rotational movement when external forces are less than its frictional limit, but allows movement of the arm when the frictional force is exceeded. Each segment 38 is free to rotate relative to adjacent segments about their common axes. A lumen (not shown) extending down the middle of the arm can house electrical wires for powering a component at the distal end (cuff 26) or house a malleable rod down the center of the elements, which may provide enhanced resistance to external forces, and provide improved stabilization. Typically, the segments 38 are made of a polyester material.

The stabilizing cuff 26 captures a tubular implement and holds it in position during a surgical procedure. At the same time, the construction of the cuff 26 provides some give to its capture of the implement, both securing it and permitting it to move into different angles.

Figure 6:
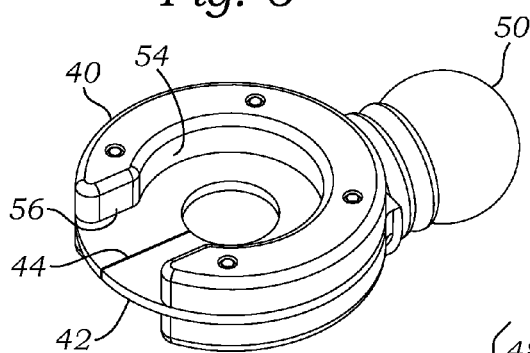
FIGS. 6 and 6A are assembled and exploded views of an exemplary cuff used on a distal end of the stabilizer of FIG. 1.
Figure 6A:
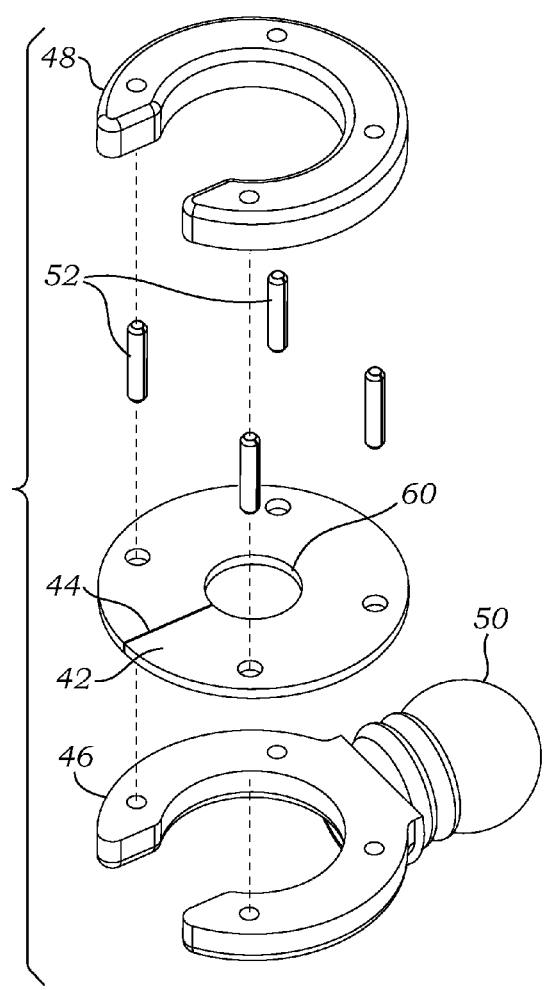

As seen best in FIGS. 6 and 6A, the stabilizing cuff 26 comprises a relatively stiff partial ring 40 (e.g., polycarbonate) and an annular disk-shaped flexible gasket 42 (e.g., silicone). The gasket 42 contains a slit 44 extending from a peripheral edge to a central aperture which allows the user to affix a sheath or instrument from a lateral, or radial, direction, rather than having to insert it longitudinally, or axially, through a complete, or closed, ring.

In one embodiment, the partial ring 40 is C-shaped and includes a lower member 46 and an upper member 48. The lower member 46 includes a top half of the C-shaped partial ring 40 and a radially-projecting ball 50, while the upper member 48 provides just the top half of the C-shaped partial ring. The members 46, 48 are preferably planar and sandwich the planar gasket 42 therebetween, the assembly being held together with adhesive or similar expedient, such as securing pins 52, which could be rivets or small screws. Preferably, the gasket includes a series of peripheral through holes (not numbered) that receive the securing pins 52 for secure fixation within the C-shaped partial ring.

As seen in FIG. 6, the C-shaped partial ring 40 defines a stiff body forming a partial enclosure 54 with an open mouth 56. The highly flexible gasket 42 is desirably disk-shaped and includes the slit 44 therein directed toward the open mouth 56. As will be see below, the open mouth 56 is sized larger than an elongated port-access device, such as an introducer having a tubular sheath, such that the cuff 26 can be pressed around the sheath which enters the slit 44 and is resiliently held by the gasket 42 which extends into the partial enclosure 54. The gasket 42 also preferably defines an inner aperture 60 concentric within the partial enclosure 54 that receives the introducer sheath and provides a centering and stabilizing force. In general, the gasket 42 is open toward the open mouth 56 with a slit, channel, aperture, etc., to receive and resiliently retain a tubular body therein.

In a preferred embodiment the C-shaped partial ring 40 is formed of a relatively stiff material such as a medical grade polymer, e.g., Delrin, while the gasket 42 is an elastomer such as silicone or polyurethane. The partial ring 40 provides a structural skeleton and the gasket 42 resiliently supports an introducer sheath to permit some movement therebetween. Both the thickness and the hardness of the elastomeric gasket 42 will change the amount of force required to insert, move (axial), and remove the sheath from the cuff 26. The axial dimension or thickness of the cuff 26 also determines the degree to which the sheath or instrument is allowed to pivot when a lateral force is applied to a remote end, as will be further explained below with reference to FIGS. 10 and 11.

Figure 5:
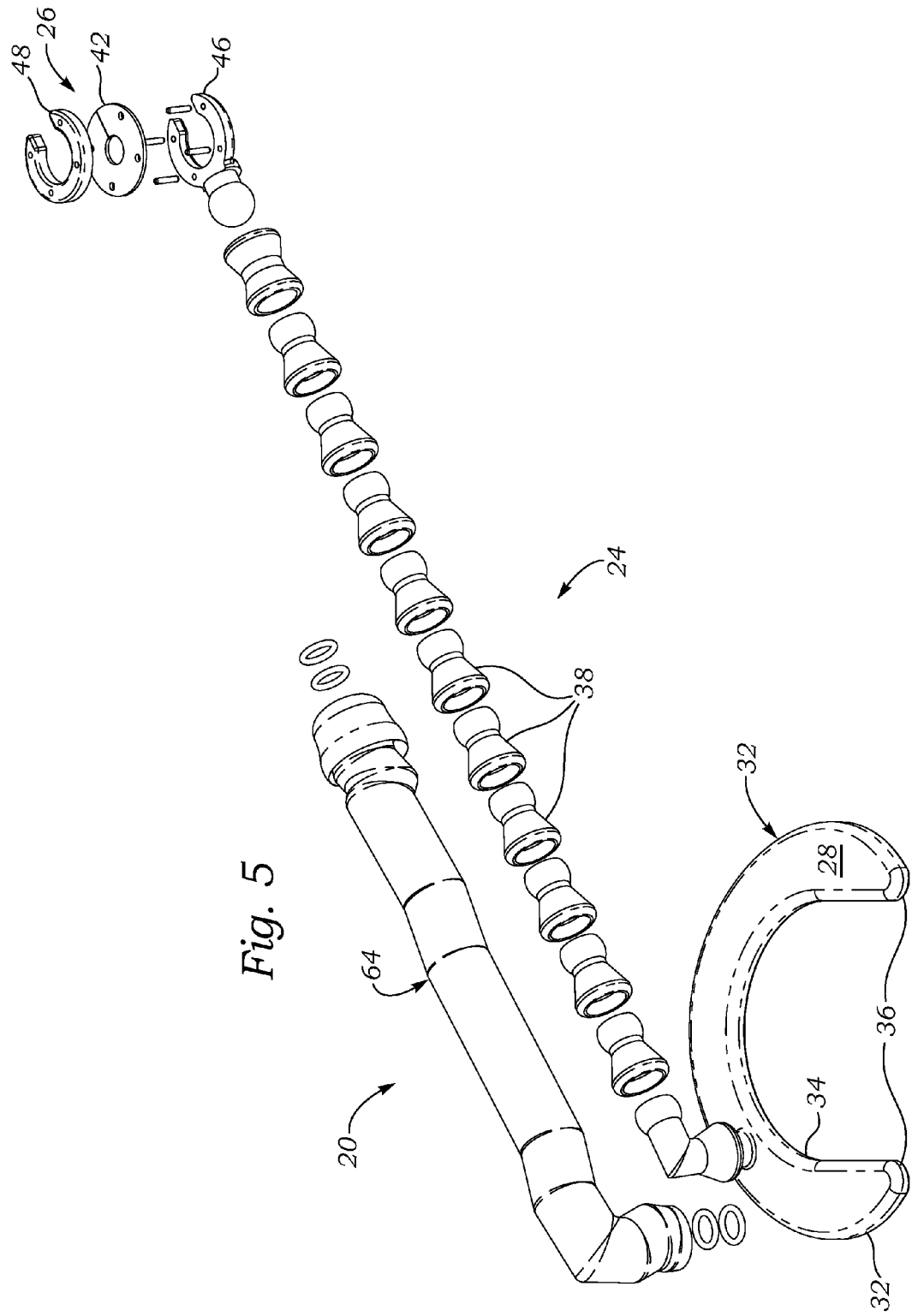
FIG. 5 is an exploded view of the stabilizer of FIG. 1 with a protective barrier.

FIGS. 5 and 7-8 illustrate an exemplary version of the intracardiac sheath stabilizer device 20, including a protective barrier 64 around the articulating arm 24 to maintain sterility. The arm 24 is shown exploded in FIG. 5 and includes a proximal elbow 70 that attaches to the base 22, the articulated segments 38, and a distal coupling member 72. It should be noted that proximal and distal in this sense refers to the relative proximity to the base 22. Each of these elements preferably connects via ball and socket couples, so that for example the ball 50 of the lower member 46 of the cuff 26 fits into a socket in the coupling member 72, as seen in cross-section in FIG. 7B. Each segment 38 includes a socket on a proximal end and a ball on a distal end, with the topmost segment ball fitting into a socket in the coupling member 72. The base 22 also has an upstanding ball 74 that fits into the socket of the lowermost segment 38, as seen in cross-section in FIG. 7A. The barrier 64 may be a flexible sheet material such as polypropylene or the like, and extends from the base 22 to the cuff 26, each end being secured with O-rings 76 as seen in FIGS. 7A and 7B.

FIGS. 9A and 9B illustrate the use of the exemplary stabilizer 20 during an intracardiac surgical procedure carried out with a port-access sheath 80 through an intercostal incision I in a chest wall CW. An intercostal incision I is formed between adjacent ribs R. A number of tissue retractors are known for holding the surrounding soft tissue back from the incision to increase access and visibility. One such "soft" retractor 82 is shown having a resilient ring 84 connected to four thin bands or straps 86 of flexible material at 90° intervals, such as a Dacron fabric. The term "soft retractor" means that the retractor has flexible, typically contoured or rounded, skin contact surfaces that "give" somewhat, and excludes purely metal retractors such as rib spreaders. The ring 84 can be compressed in its plane to form an elongated shape that can pass through the incision I to the inside of the chest wall CW, whereupon it springs back to its original shape and is retained by the ribs R within the chest cavity. The straps 86 are then draped out of the incision I across the exterior surface of the chest wall CW and secured with adhesive or the like. The retractor is shown in greater detail in U.S. Pat. No. 6,814,700 to Mueller, et al., the disclosure of which is incorporated by reference herein.

The stabilizer 20 is held firmly by the soft tissue retractor 80, thus utilizing an existing device in the surgery and eliminating the need for a separate clamp. Specifically, the straps 86 extend over the base 22 and constrain the base against the exterior surface of the chest wall CW. In the illustrated embodiment, the base 22 is C-shaped and extends approximately 270° around, so that only three of the four straps 86 are needed to secure it around the incision I. The open nature of the base 22 permits a surgeon to easily insert it under pre-installed straps 86, though a full circular base may also be used with all four straps 86 capturing it. Also, a partial-circular shape reduces the device profile, which is important in restricted spaces, for example, when working adjacent to a large breast or abdominal panniculus.

Figure 2:
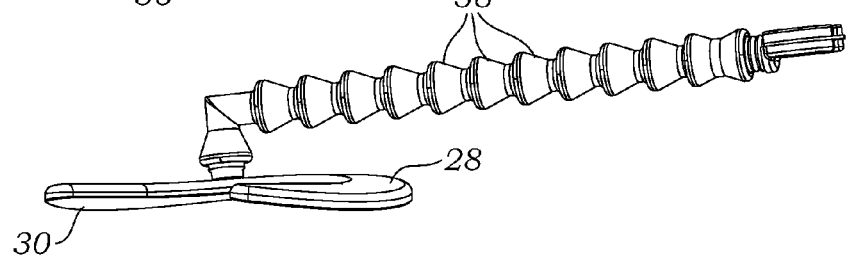
Figure 3:
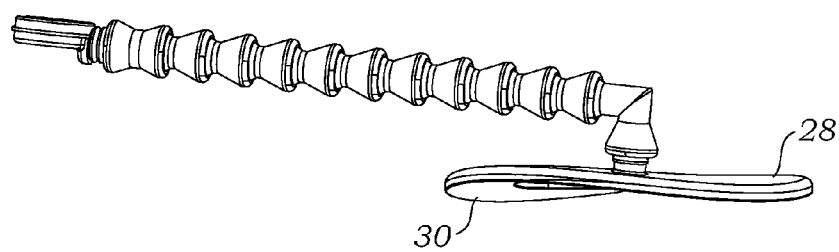
Figure 4:
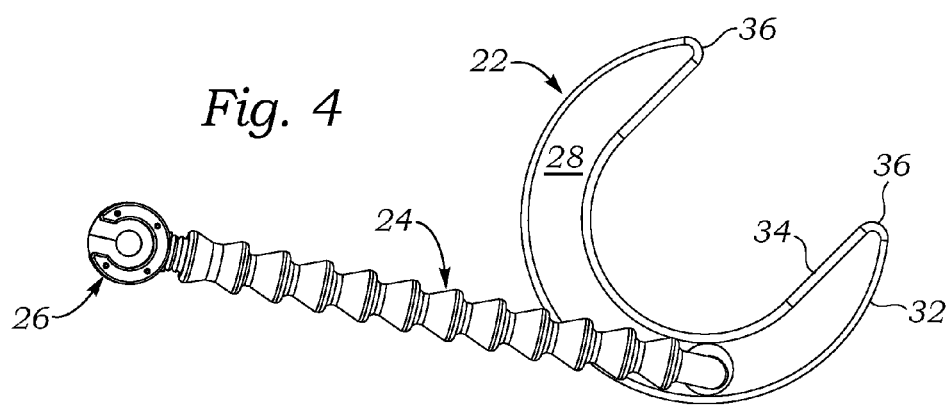

The base 22 is held generally parallel to the chest wall CW such that the articulated arm 24 initially projects perpendicularly away therefrom. The base 22 is preferably contoured to accommodate the shape of the patient's surface anatomy, such as having a concave lower surface as shown in FIGS. 2 and 3. Due to the high degree of malleability and rotatability of the arm 24, the cuff 26 may be positioned and angled in a desired way to optimally receive the tubular sheath 80. The stabilizer 20 thus provides a firm yet resilient support for a proximal mid-portion of the sheath 80, holding it at a desired angle for the particular surgery.

Other embodiments of the base 22 include construction from a malleable material that allows the user to manually shape the base into a variety of configurations, rubberizing the base 22 to provide increased friction at the interface between the patient and retractor, thus improving stability, and integrating the retractor 82 itself into the base 22, or vice versa. Alternatively, a miniaturized design can permit positioning of the base within the tissue planes of the anatomic region of interest, for example, the chest wall or skull, which allows the base 22 to be compressed between the layers of the chest wall or skull by the metal or soft-tissue retractor, thereby providing enhanced stabilization.

The arm 24 can be articulated into a position that accommodates the natural angle of the sheath and patient's anatomy, and the sheath can then be constrained, for example "snapped," into the cuff 26. Adjustments can be made to the articulation/positioning at any time, without a loosening/locking mechanism.

As mentioned, the stabilizer 20 may be used for a number of procedures, but is particularly well-suited for stabilizing an introducer sheath 80 for intracardiac surgery. The sheath 80 includes a proximal housing 90 within which is positioned a seal that permits passage of devices or instruments for operating inside the heart. One such procedure will be described below.

Figure 10:
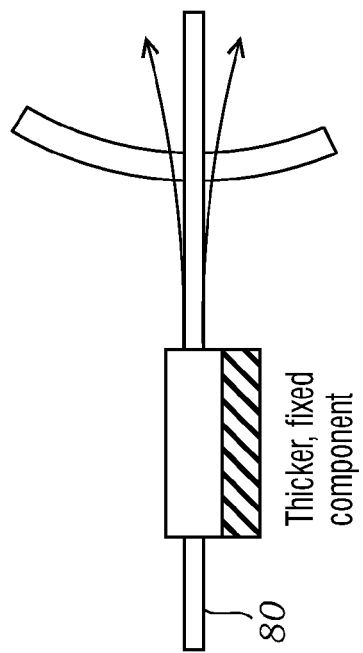
FIG. 10 is schematic view of the beneficial stabilizing effect of the stabilizer of FIG. 1 when used to hold a port-access intracardiac sheath.

FIG. 10 is schematic view of the stabilizer 20 holding a port-access intracardiac sheath 80 that projects through the heart wall. The motion of the heart wall is shown displacing the right end of the sheath, but because of the resilient capture of the sheath by the cuff, the motion on the proximal (left) end of the sheath is much smaller. The cuff provides both a pivot point and a damping effect to the sheath, greatly reducing its movement outside of the body. In addition, the distal end of the sheath 80 is to a large extent free to move with the heart wall, thus reducing trauma thereto.

Figure 11:
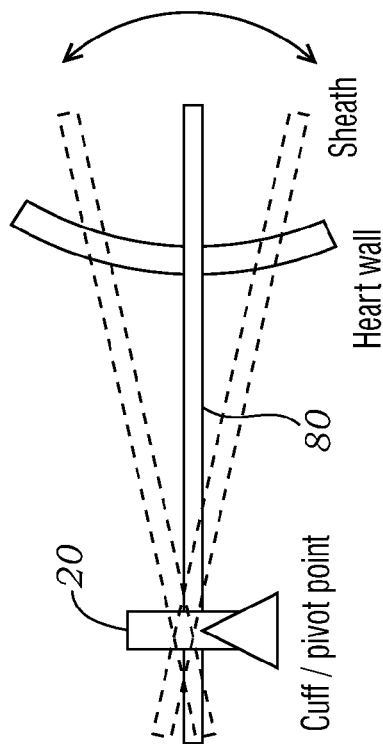
FIG. 11 is schematic view of movement of a port-access intracardiac sheath when held by a rigid stabilizer of the prior art.

On the other hand, FIG. 11 shows a port-access intracardiac sheath 80 when held by a more rigid stabilizer of the prior art. The proximal end is held firm, which resists movement of the heart wall, potentially causing trauma thereto. During a transapical cardiac procedure, where a sheath is placed into the ventricular cavity through a dilated puncture/incision, a sheath that is completely immobilized by a device/retractor can cause trauma to the heart tissue, and consequent bleeding around the sheath, due to the rhythmic, lateral motion of the heart relative to the sheath. As seen in FIG. 10, the cuff 26 acts as a pivot point in which one end of the sheath moves with the heart, rather than relative to the heart. Less relative motion predicts less tissue trauma and bleeding.

Figure 12:
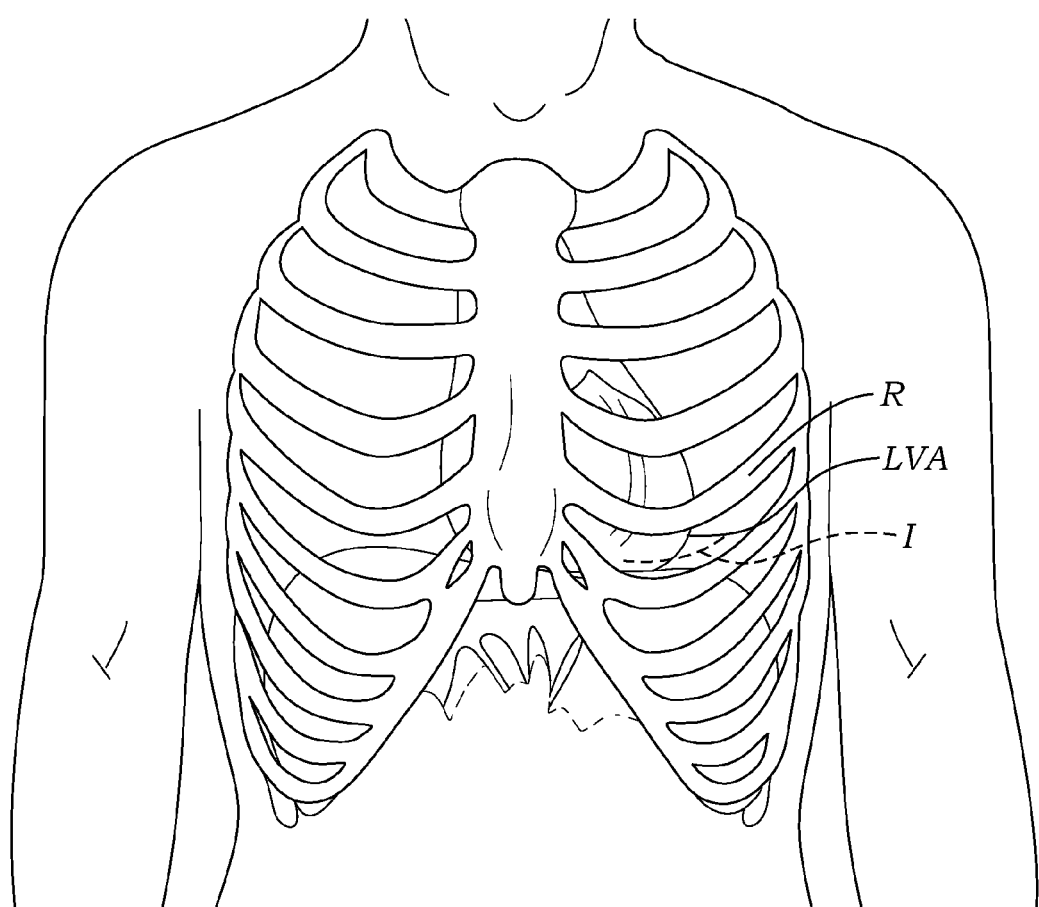
FIG. 12 is a schematic frontal view of a patient showing the location of an intercostal incision providing access to the apex of the left ventricle of the heart.
Figure 13:
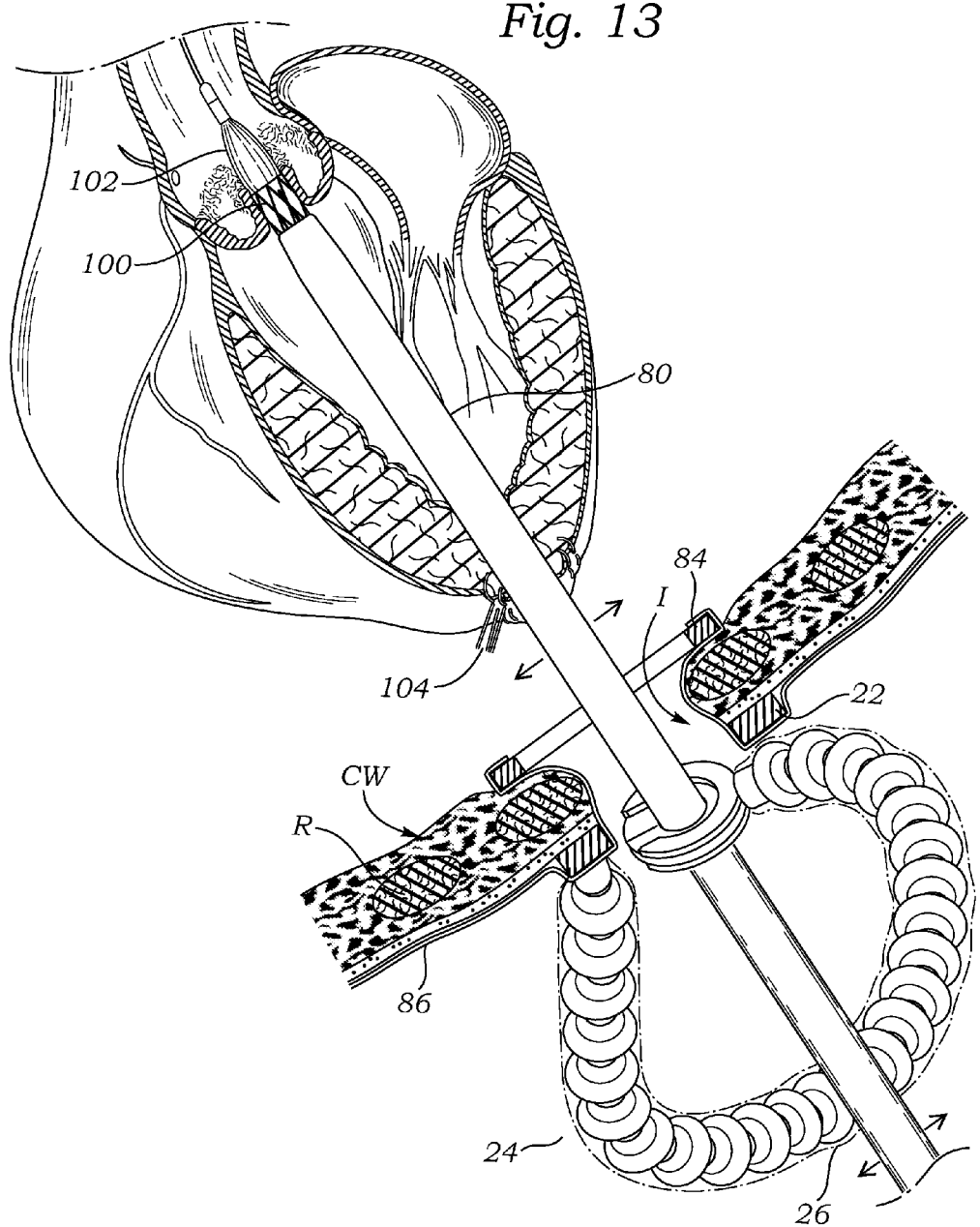
FIG. 13 is a cross-sectional view through the left side of a patient's heart showing a transapical procedure for implanting a prosthetic heart valve assisted by an intracardiac stabilizer disclosed herein.

With reference now to FIGS. 12 and 13, a preferred method of deploying and implanting a prosthetic heart valve of the present invention using a transapical approach will now be described in more detail. The devices and methods disclosed herein are particularly well-suited for replacing a stenotic aortic valve, and as such a valve annulus pre-dilation procedure typically precedes the valve implantation so as to smooth out the contours of the annulus and leaflets. It should be noted, however, that the procedure described herein may be performed without valve pre-dilation.

Furthermore, the present procedure may be performed as a first time valve implant or to supplement a previous implant. A relatively large proportion of recipients of prosthetic heart valves are older, typically older than 60. Over time, prosthetic heart valves have been known to show reduced performance and even failure. Re-operating on septuagenarians and even octogenarians is problematic. However, a port access procedure such as disclosed herein eliminates open-heart surgery and potentially cardiopulmonary bypass, and is therefore more desirable for the aging patient. Therefore, the present invention contemplates transapical implantation of a prosthetic heart valve over an existing prosthetic valve implant. In such a case, a pre-dilation step is typically not necessary, though it is conceivable.

The prosthetic heart valve implantation procedure described herein may be performed in conjunction with cardiopulmonary bypass, or without bypass in a so-called off-pump procedure. The necessity for bypass depends on a number of factors, including the patient's age, vulnerability to such a procedure, and viability of the native leaflets. Ideally, the implantation procedure is performed off-pump.

One surgical procedure that utilizes the devices of the present application is a transapical heart valve replacement through the left ventricular apex, as disclosed in U.S. application Ser. No. 12/821,628, filed Jun. 23, 2010, the disclosure of which is expressly incorporated herein. First, the prosthetic heart valve and various delivery instruments are selected and prepared for use by removing them from any packaging and rinsing or sterilizing as needed. A prosthetic heart valve 100 is then crimped over a balloon 102 on a catheter.

An intercostal incision I in the chest wall CW between two ribs R and over the left ventricular apex LVA is created, as seen in FIG. 12. The resilient ring 84 and straps 86 of the soft tissue retractor 82 (FIG. 13) may be installed to hold back the tissue surrounding the incision I, thus enhancing access and visibility to the left ventricular apex LVA.

Next, as seen in FIG. 13, the surgeon installs one or more purse-string sutures 104 in the tissue of the left ventricular apex prior to formation of an initial puncture in the heart wall. In a preferred embodiment, the surgeon places a first line of purse-string sutures generally in a first circle in one direction, and then places a second line of purse-string sutures generally in a circle concentric to the first circle but in an opposite direction. The result is two concentric circles of separate purse-string sutures defining a periphery within which the puncture is formed. The purse-string sutures can therefore be pulled to cinch the ventricular tissue around whatever object passes through the puncture. In particular, the purse-string sutures are tightened around both a guidewire and introducer sheath 80.

The surgeon introduces a guidewire through a pre-formed apical puncture in the left ventricle LV and within the purse string sutures, through the native aortic valve AV and into the ascending aorta AA. A pre-dilation step of the annulus may be performed to enlarge or crack existing calcification in the aortic annulus. The surgeon then inserts a dilator and introducer sheath 80 into the LV through the apical puncture as an access port.

At this point the stabilizer 20 of the present application may be installed by mounting it to a stationary object, such as the soft tissue retractor 82. The stabilizer 20 may also be installed at the time of securing the soft tissue retractor 82.

The balloon catheter is advanced over the guidewire and through the introducer sheath 80. The surgeon locates the prosthetic heart valve 100 at the aortic annulus and between the native aortic leaflets. Radiopaque markers may be provided on the distal tip of the introducer sheath to more accurately determine its position relative to the valve and balloon. When the surgeon is satisfied of the proper positioning and rotational orientation of the valve, as seen in FIG. 13, the balloon 102 is expanded into contact with the annulus.

The surgeon then deflates the balloon 102 and withdraws the entire delivery system including the balloon catheter over the guidewire. The introducer sheath 80 is withdrawn, followed by the guidewire. Ultimately, the purse-string sutures previously described are cinched tight and tied to close the puncture.

Up to this point a single-arm stabilizer 20 has been described as a basic embodiment of the invention. At least one stabilizing arm such as arm 24 with cuff 26 is provided on the base 22, though more than one arm may be preferred by some surgeons. Accordingly, FIGS. 14-18 illustrate an exemplary dual-arm surgical stabilizer 120 comprising a base 122, a first articulated arm 124 attached thereto having a stabilizing cuff 126, and a second articulated arm 127 also attached to the base having a clip 128. The provision of two stabilizing arms enhances the ability of the stabilizer 120 to hold and maintain the position of a surgical instrument such as an introducer sheath, as will be described below. In some instances, more than two stabilizing arms may be called for, and accordingly the present invention is not limited to just one- or two-arm systems. Also, more than one surgical instrument may be stabilized. For example, two arms may stabilize a primary instrument while a third arm stabilizes a secondary instrument, such as a light probe.

Figure 15:
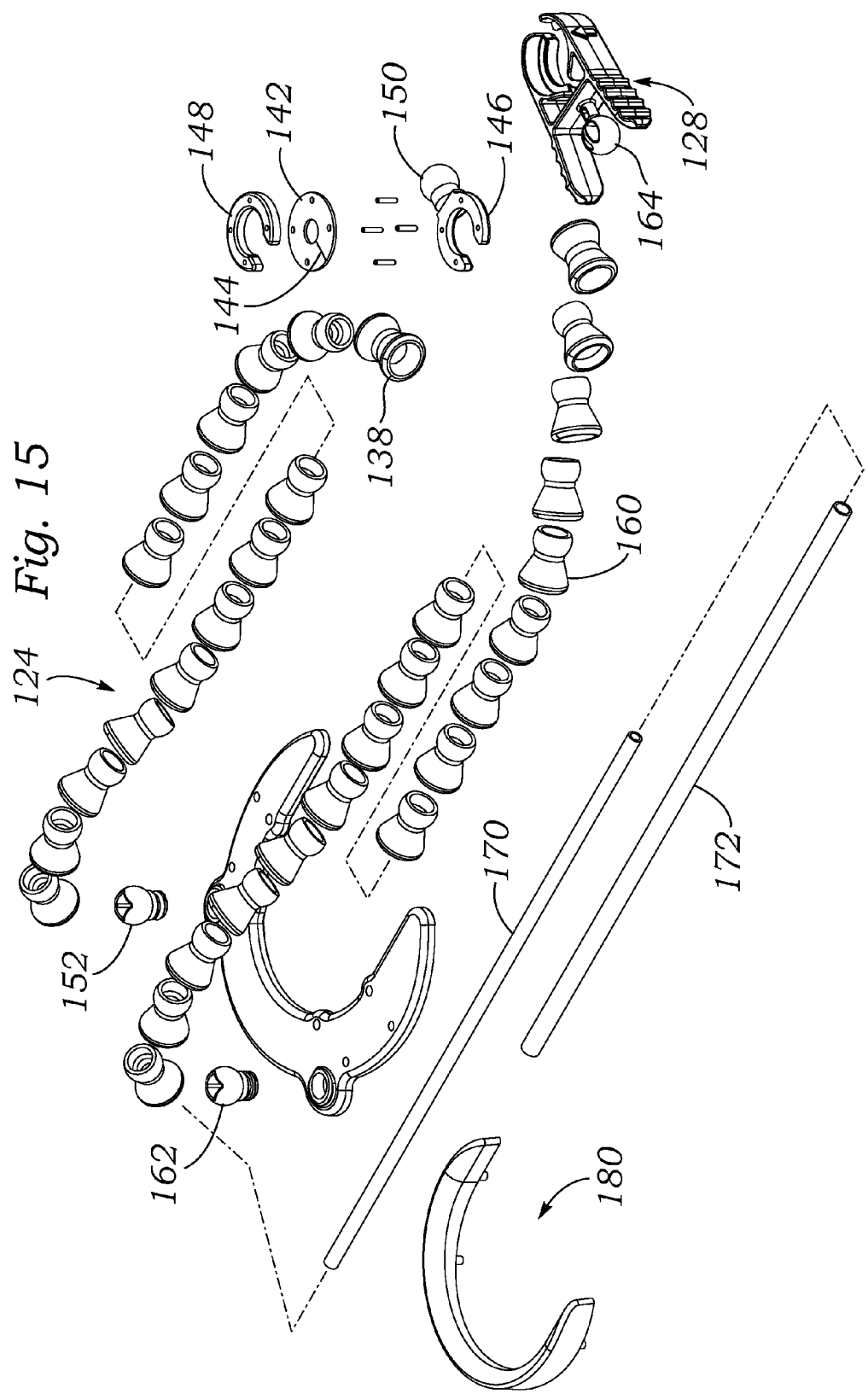
FIG. 15 is an exploded perspective view of the stabilizer of FIG. 14A.

As in the earlier embodiment, the base 122 provides a structural brace adapted to be held by or adjacent to an existing stationary anchor in the surgical field. As best seen in FIG. 15, the base 122 preferably comprises a C-shaped body having a somewhat planar cross-section with an upper face 129, a lower or contact face 130 (see FIG. 16), a convex outer edge 132, and a concave inner edge 134. The outer edge 132 and inner edge 134 converge in two tips 136. The base 122 is formed of a polymer, and preferably has a soft outer polymer surface and an inner malleable member, such as rubber coated metal like a silicone coated Stainless Steel. In a preferred embodiment, the C-shaped body is a rubber coated metal with a slightly concave curvature toward the contact face 130, that can be shaped as needed per application.

The articulated arm 124 may be provided in a number of different forms that provide rigidity or stability to a tubular implement held by the stabilizer 120, while also enabling easy manipulation to reposition the implement. Articulated arms are well known in the art, and the illustrated embodiment includes a plurality of linked segments 138 that are coupled through a ball joint or other similar three-dimensional structural connection. Of course, a simple malleable arm may also be used with some loss of fine control, but the purpose of three-dimensional variation remains. The arm 124 is desirably made in the same manner as the single articulated arm 24 seen in FIGS. 1-5, and may also be referred to herein as a proximal stabilizing arm.

The construction of the stabilizing cuff 126 enables resilient capture of a tubular implement to hold it in position during a surgical procedure without unduly restricting movement such as generated by a beating heart. As seen best in FIG. 15, the stabilizing cuff 126 comprises a relatively stiff partial ring formed from a lower member 146 and an upper member 148, and an annular disk-shaped flexible gasket 142 therebetween. The gasket 142 contains a slit 144 extending from a peripheral edge to a central aperture which allows the user to affix a sheath or instrument from a lateral, or radial, direction, rather than having to insert it longitudinally, or axially, through a complete, or closed, ring. As in the earlier embodiment, the stabilizing cuff 126 includes a ball joint 150 that couples to one of the articulated segments 138 in the arm 124 and facilitates rotational and angular freedom of movement.

FIG. 15 also shows that a proximal end segment 138 mates with a ball connector 152 that threads into an aperture in the base 122. The ball connector 152 projects straight up from the generally planar base 122 in contrast to the elbow connector shown in the earlier one-arm stabilizer 20. This is believed to provide better adjustability of the angle of the first stabilizing arm 124.

Figure 14A:
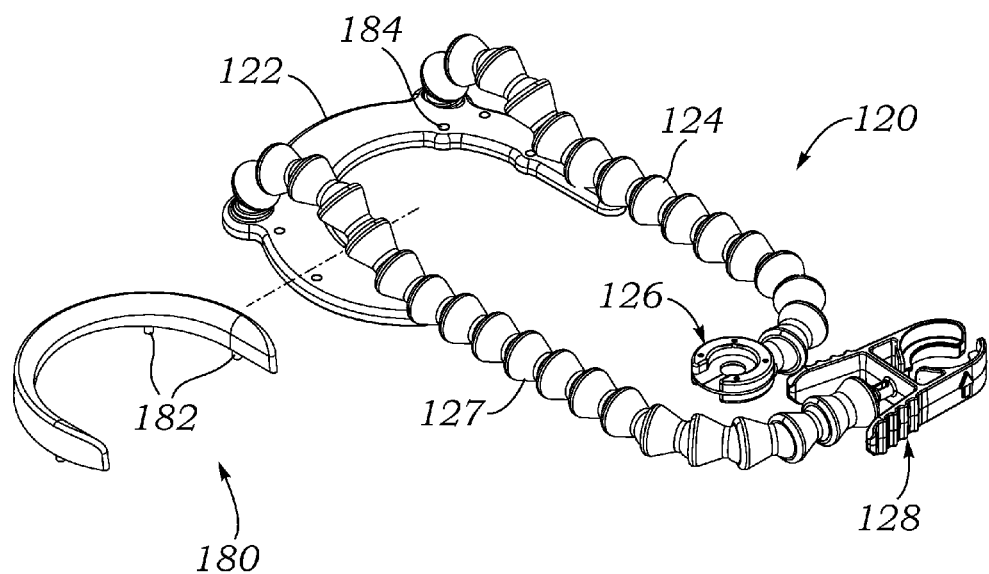
FIG. 14A is a perspective view of an alternative intracardiac stabilizer of the present application having dual articulated arms, and a C-shaped adapter for assembly with the stabilizer to facilitate use in conjunction with certain types of tissue retractors.

Still with reference to FIG. 15, the second stabilizing arm 127 also includes a plurality of connected articulated segments 160 that mate on a proximal end to a ball connector 162 threaded into the base 122, and on a distal end to a ball 164 provided on the back end of the clip 128. The assembled arm 127 is seen in FIG. 14A. Although the clip 128 is shown, a cuff identical to the cuff 126 on the first arm may be used, as may a different instrument for temporarily securing the distal end of the arm 127 to a surgical instrument such as an introducer sheath. The clip 128 shown features a pair of facing concave jaws 166 that may be spread apart by squeezing a pair of resilient fingers 168 connected thereto. The concave jaws 166 are sized to removably capture a part of the surgical instrument, such as a proximal introducer housing as will be seem below. Because the second stabilizing arm 127 typically secures a proximal end of the instrument, it is also termed a proximal arm. The clip 128 may be made of a more rigid material such as polycarbonate as there is less need for a flexible anchor at the proximal end of an introducer. Although there is some possible movement from the length of the arm 127, the clip 128 essentially rigidly clamps a proximal end of the introducer rending it relatively stationary. At a minimum, the clip 128 desirably greatly inhibits if not eliminates axial movement of the introducer, which is why it is shown in FIGS. 19 and 20 fastened to a proximal hub structure and not the sheath itself.

In terms of flexibility, the first or distal stabilizing arm 124 may be identical to the second or proximal stabilizing arm 127, with the swivel-connected segments 138 and 160 providing nearly unlimited articulation with a small amount of frictional resistance to movement. However, a preferred embodiment of the dual-arm stabilizer 120 includes one arm stiffer than the other, in particular, the proximal arm 127 is desirably stiffer than the distal arm 124. There are numerous ways to provide stiffness to an articulated arm, and the illustrated embodiment should not be considered limiting.

Figure 18:
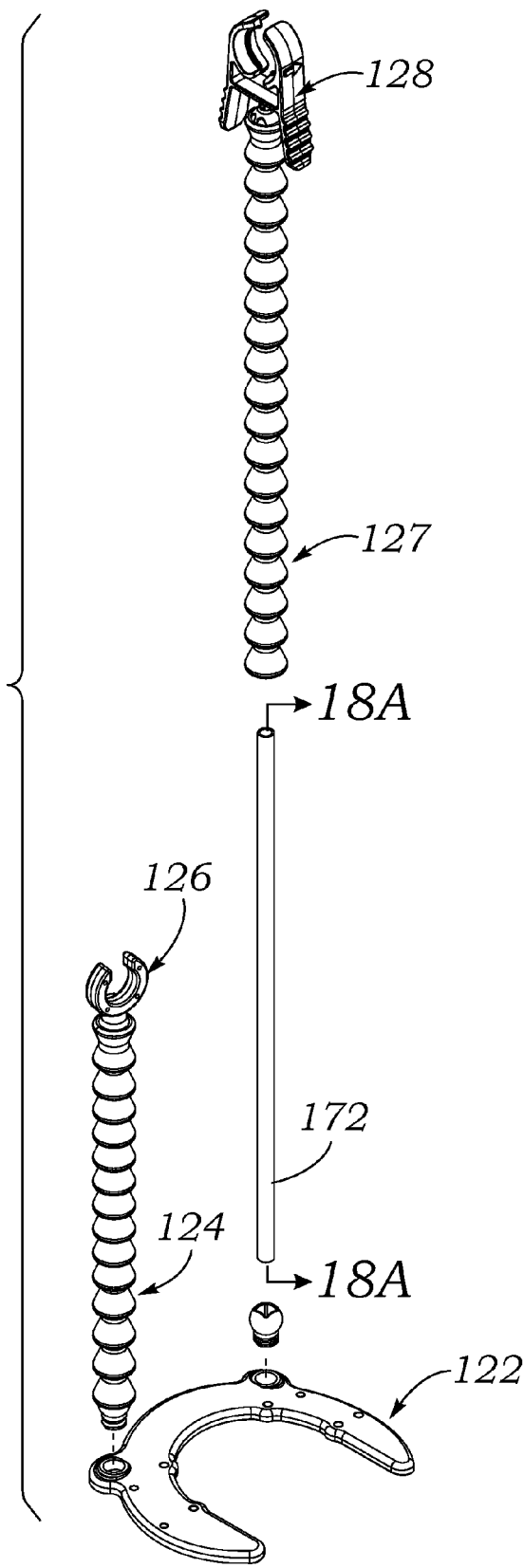
FIG. 18 is an exploded perspective view of the stabilizer of FIG. 14A illustrating inner tubes of the longer stabilizing arm
Figure 18A:
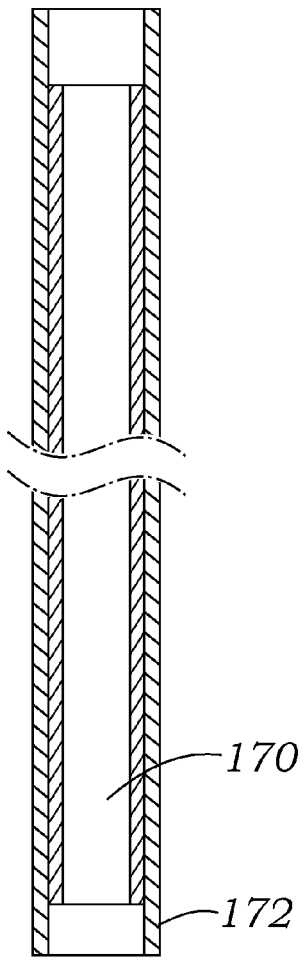

In one embodiment, as seen in FIGS. 17-18, two concentric tubes 170, 172 provide rigidity to the articulated segments 160 of the proximal stabilizing arm 127. Each segment 160 is hollow and together the segments provide a through lumen in the arm 127. An inner tube 170 closely receives an outer tube 172 that fits closely within the through lumen, as seen in cross-section in FIGS. 17A and 17B. The inner tube 170 is made of a malleable or plastically-deformable material such as aluminum, while the outer tube 172 is a frictional elastomer such a Pelethane. The malleable inner tube 170 provides greater stiffness to the arm 127 and permits the user to place it in a position where it will remain under larger applied loads forces than before. For instance, the arm 127 is typically used to hold the proximal end of an introducer sheath which includes a bulky housing that weighs more than the sheath itself.

Advantageously, the outer tube 172 provides an interface between the articulating segments 160 and the inner tube 170 that prevents the inner tube from causing the arm 127 to bend in one direction and then rotate while maintaining that angulation. That is, a malleable tube by itself may tend to form a bend and maintain that bend upon further application of forces, rotating about a proximal extent of the bend by virtue of low frictional resistance to swiveling of the articulated segments. In other words, a malleable tube by itself may resist omni-directional bending. With the presence of the frictional outer tube 172, the tendency of the inner tube 170 to form such bends is greatly reduced because the articulated segments remain rotationally constrained by the outer tube interface. The frictional resistance to the segments swiveling is increased relative to just an aluminum inner tube.

The relative lengths of the first arm 124 and second arm 127 is seen in FIGS. 16 and 17. In particular, one arm, in this case the first or distal arm 124 has a length l that is shorter than the length L of the second or proximal arm 127. As mentioned, the first arm 124 desirably includes the cuff 126 which provides a flexible capture of a distal end of a surgical instrument. In the case of an intracardiac introducer sheath, the cuff 126 provides stability without fixing the introducer sheath too rigidly, thus permitting some movement from the patient's heart movement. On the other hand, the longer proximal arm 127 includes the more rigid hold of the clip 128, suitable for stabilizing a proximal end of the instrument in a more stationary position. Of course, as mentioned, a cuff can be used on both arms as well. An exemplary length l for the shorter distal arm 124 is between about 8-9 inches, while proximal arm 127 preferably has a length L of about 10-11 inches or greater. The shorter distal arm 124 is also more difficult to bend and thus less susceptible to dislodgment in use, so a rigidifying insert is not as necessary.

The stabilizers of the present application advantageously mate with a plurality of stationary anchors in the surgical field. The one-arm embodiment described above was shown in FIGS. 9A and 13 coupled to a soft tissue retractor available from Edwards Cardiovations. FIG. 19 below shows the stabilizer 120 working in conjunction with a metallic spreader, and FIG. 20 shows it with still another soft retractor.

Figure 14B:
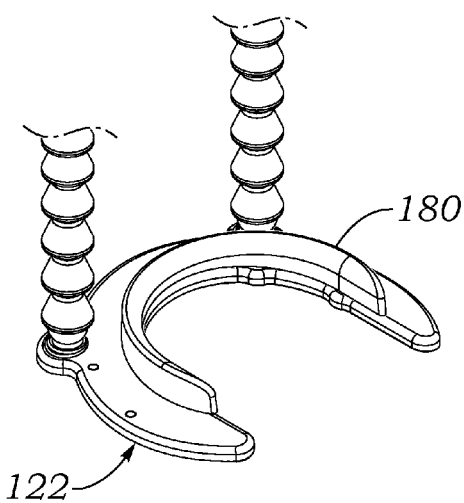
FIG. 14B is a partial perspective view of a base of the stabilizer of FIG. 14A and the C-shaped adapter assembled thereon.

With reference to FIGS. 14-15, a C-shaped adapter 180 is shown that may be packaged with the stabilizer 120 (or stabilizer 20 shown above) for use with certain soft retractors. The adapter includes a plurality of downwardly-directed pegs that fit within an identical pattern of holes 184 on the top surface of the base 122. FIG. 14B shows the adapter 180 assembled on top of the base 122 in a position close to the inner edge thereof. The adapter 180 has a height somewhat greater than the relatively flat base 122 so as to form a raised lip on the inside edge of the base. The C-shaped adapter 180 is desirably made of the same material as the base 122, both typically Acrylonitrile-Butadiene-Styrene (ABS).

FIG. 19 shows the exemplary dual-arm stabilizer 120 in use in conjunction with a metallic chest spreader 190 such as available from Estech or Finni. The spreader 190 holds open adjacent ribs to form an aperture through which a sheath 192 of an introducer and other surgical instruments (not shown) may be passed. The introducer further includes a proximal hub or housing 194 typically enclosing a hemostatic valve through which secondary instruments such as balloon catheters may be passed. This configuration may be used for intracardiac procedures, such as a transapical heart valve replacement operation.

The base 122 of the dual-arm stabilizer 120 fits closely around the spreader 190 and is stabilized thereby. In one embodiment the arms of the spreader 190 are cranked open against the inner edge of the base 122 for stability. Alternatively, temporary sutures may be installed to the patient's chest through auxiliary holes in the base 122, as seen in FIGS. 14A and 14B. IN a number of ways the base 122 is stabilized around the chest opening.

The surgeon manipulates the distal arm 124 so that the cuff 126 holds a distal portion of the sheath 192 close to the chest opening. The surgeon attaches the clip 128 on the proximal arm 127 to the introducer hub 194 some distance above the chest opening. In this way, the angle of the introducer may be easily changed and then held in place by the two arms of the stabilizer 120. Moreover, the distal cuff 126 relatively flexibly retains the distal portion of the sheath to permit some movement from beating heart movement, thus reducing trauma to the left ventricular apex and puncture wound therein. The less flexible second arm 127 provides greater support for the relatively heavier proximal end of the introducer, and holds the hub 194 more rigidly with the clip 128 because a flexible hold is not so important at that location.

Now with reference to FIGS. 20 and 21, a still further configuration of the stabilizer 120 that utilizes the C-shaped adapter 180 is shown. A soft retractor 200 shown in FIG. 21 is installed at the chest opening. The retractor 200, available from Applied Medical of Santa Margarita, Calif., under the trade name Alexis includes an elastic outer ring 202 and an elastic inner ring 204 joined together by a flexible tube. The inner ring 204 is squeezed and fit through the chest aperture, expanding on the inside of the rib cage much like the soft retractor 82 shown in FIG. 13. The stabilizer base 122 with the adapter 180 assembled thereon is placed around the chest opening, and the outer ring 202 is pulled up and over the adapter, as shown, thus mutually securing both elements. The raised lip formed by the adapter 180 on the base 122 provides a convenient catch to hold the outer ring 202 in place. At the same time, the stabilizer 120 is held stationary around the chest opening. This assembly is highly stable and presents a very low profile to enhance visibility and access through the chest opening. The combination is easy to install and easy to re-orient the stabilizer 120 if necessary.

As in FIG. 19, the first or distal arm 124 and cuff 126 stabilize a distal portion of the introducer sheath 192. The second or proximal arm 127 and an alternative clip 128' brace the introducer hub 194. The alternative clip 128' includes a simple resilient C- or U-shaped member with a shape that retains the hub 194 until force is applied by the user.

While the invention has been described in its preferred embodiments, it is to be understood that the words which have been used are words of description and not of limitation. Therefore, changes may be made within the appended claims without departing from the true scope of the invention.

What is claimed is:

1. A surgical stabilizer for use with a surgical site retractor and an elongated port-access device having a tube, comprising:
    a base defining a periphery having a size that enables it to be held against an exterior chest wall by the surgical site retractor and around an intercostal chest incision with the base extending over a first rib on a first side of the intercostal chest incision while simultaneously extending over a second rib on a second side of the intercostal chest incision, wherein the first side is opposite to the second side;
    a first arm attached to and extending away from the base and capable of being bent into and retaining a variety of shapes; and
    a distal cuff attached to the first arm opposite the base, the cuff having a stiff C-shaped partial ring and a flexible gasket held across an area defined within the C-shaped partial ring, the gasket having a slit directed toward an open mouth of the C-shaped partial ring, the open mouth being sized larger than the tube of the port-access device such that the cuff can be pressed around the tube, or vice versa, with the tube entering the slit and being resiliently held by the gasket.

2. The stabilizer of claim 1, wherein the cuff gasket defines an inner aperture smaller than the C-shaped partial ring, the slit connecting to the inner aperture.

3. The stabilizer of claim 1, wherein the cuff C-shaped partial ring includes a C-shaped lower member attached to a C-shaped upper member, and the gasket is sandwiched therebetween.

4. The stabilizer of claim 1, wherein the base defines a C-shaped body with an upper face and a concave lower contact face.

5. The stabilizer of claim 4, wherein the C-shaped body has an outer surface of soft polymer and includes an inner malleable member able to conform to three-dimensional surfaces.

6. A surgical stabilizer for use with a flexible ring-shaped surgical site retractor and an elongated port-access device having a tube, comprising:
    a base defining a periphery having a size that enables it to be held against an exterior chest wall by the flexible ring-shaped surgical site retractor and around an intercostal chest incision with the base extending over a first rib on a first side of the intercostal chest incision while simultaneously extending over a second rib on a second side of the intercostal chest incision, wherein the first side is opposite to the second side, the base comprising a semi-circular C-shaped portion configured to encircle most of the chest incision and to lie on top of the flexible ring-shaped surgical site retractor;
    a first arm attached to and extending away from the base and capable of being bent into and retaining a variety of shapes; and
    a distal cuff attached to the first arm opposite the base, the cuff configured to receive and resiliently hold a tube therein.

7. The stabilizer of claim 6, wherein the cuff comprises a stiff C-shaped partial ring and a flexible gasket held across an area defined within the C-shaped partial ring, the gasket having a slit directed toward an open mouth of the C-shaped partial ring, the open mouth being sized larger than the tube of the port-access device such that the cuff can be pressed around the tube, or vice versa, with the tube entering the slit and being resiliently held by the gasket.

8. The stabilizer of claim 7, wherein the cuff gasket defines an inner aperture smaller than the C-shaped partial ring, the slit connecting to the inner aperture.

9. The stabilizer of claim 7, wherein the cuff C-shaped partial ring includes a C-shaped lower member attached to a C-shaped upper member, and the gasket is sandwiched therebetween.

10. The stabilizer of claim 6, wherein the base defines a malleable C-shaped body with an upper face and a concave lower face.

11. The stabilizer of claim 10, wherein the C-shaped body is formed as a single unitary body.

12. The stabilizer of claim 10, wherein the C-shaped body has an outer surface of soft polymer and includes an inner malleable member able to conform to three-dimensional surfaces.

13. The stabilizer of claim 6, wherein the stabilizer base includes a C-shaped raised lip around an inner edge surrounding the open area.

14. The stabilizer of claim 13, wherein the raised lip is formed by a C-shaped adapter removably attached to an upper surface of the base.

* * * * *